(12) United States Patent
Terabe

(10) Patent No.: US 7,144,112 B2
(45) Date of Patent: Dec. 5, 2006

(54) OPTOMETRIC APPARATUS

(75) Inventor: Hirohisa Terabe, Toyokawa (JP)

(73) Assignee: Nidek Co., Ltd., Gamagori (JP)

( * ) Notice: Subject to any disclaimer, the term of this patent is extended or adjusted under 35 U.S.C. 154(b) by 257 days.

(21) Appl. No.: 10/764,458

(22) Filed: Jan. 27, 2004

(65) Prior Publication Data
US 2004/0184001 A1 Sep. 23, 2004

(30) Foreign Application Priority Data
Jan. 29, 2003 (JP) .............................. 2003-019960

(51) Int. Cl.
*A61B 3/028* (2006.01)
*A61B 3/02* (2006.01)
*A61B 3/04* (2006.01)

(52) U.S. Cl. ...................... 351/233; 351/234; 351/235; 351/216; 351/217

(58) Field of Classification Search ................. 351/235, 351/216, 217, 233, 234
See application file for complete search history.

(56) References Cited
U.S. PATENT DOCUMENTS
3,891,311 A 6/1975 Fletcher et al.
4,496,226 A * 1/1985 Augusto et al. ............ 351/235
6,048,064 A 4/2000 Hosoi et al.

FOREIGN PATENT DOCUMENTS
| DE | 90 05 493 U | 10/1990 |
|---|---|---|
| EP | 0 070 333 A2 | 1/1983 |
| EP | 0 502 413 A2 | 9/1992 |
| JP | A 64-20824 | 1/1989 |

\* cited by examiner

*Primary Examiner*—Charles A Marmor, II
*Assistant Examiner*—John R Sanders
(74) *Attorney, Agent, or Firm*—Oliff & Berridge, PLC

(57) ABSTRACT

An optometric apparatus (2) includes a rotary prism (136a, 136b) disposed in front of the eye (E), for adding a prism degree to the eye (E); a rotation device including a pulse motor (181, 184) and a rotation transmitting mechanism (146, 147, 176, 176a, 177, 177a, 178, 179, 182, 183, 185, 186) for transmitting rotation of the pulse motor to the rotary prism, the rotation device being adapted for rotating the rotary prism to change the prism degree; a command device (43a, 43b) for generating a command signal to start and stop the rotation of the rotary prism; and a control unit (60) for controlling the rotation device to drive the pulse motor to rotate at a speed of 5 pulses/sec. or more when the control unit receives the rotation start command signal until when receives the rotation stop command signal, and, to change the prism degree at a speed of 0.1 to 1.0 prism/sec.

4 Claims, 4 Drawing Sheets

OPTOMETRIC APPARATUS

BACKGROUND OF THE INVENTION

1. Field of the Invention

The present invention relates to an optometric apparatus appropriate for examining visual functions of an eye of an examinee.

2. Description of Related Art

There is an optometric apparatus for subjectively examining visual functions of an examinee's eye such as a refractive power by selectively placing optical elements having various optical characteristics to be disposed in a test window to present various kinds of optotypes through the test window to the examinee's eye. This type of optometric apparatus is constructed to change a prism degree (prism power) to be added to the eye, namely, to be disposed in the test window, thus enabling examinations of visual functions such as heterophoria, divergence, convergence, and so on. To provide a prism degree for the eye, the apparatus is provided with a pair of rotary prisms placed to be mutually independently rotatable about an examination optical axis of the test window.

In the above conventional apparatus, the rotary prisms are rotated by a pulse motor. However, a rotation step angle of a low-cost pulse motor is as large as 7.5°, so that a change step of the prism degree is as large as 0.1 prism. Further, a switch signal for changing the prism degree would be transmitted after a changed prism degree is displayed in an indicator or transmitted as a data signal representing for example the prism degree, thus taking much time to drive the pulse motor. In addition, the prism degree is changed intermittently in steps of 0.1 prism and therefore the prism degree could not be changed smoothly as compared with a manual optometric apparatus. Consequently, the above apparatus would be difficult to use in especially a divergence examination and a convergence examination which need smooth changing of the prism degree.

SUMMARY OF THE INVENTION

The present invention has been made in view of the above circumstances and has an object to overcome the above problems and to provide an optometric apparatus which can achieve smooth changing of a prism degree and allow correct examinations of visual functions.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optometric apparatus for subjectively examining visual functions of an eye of an examinee, the apparatus including: a rotary prism disposed in front of the eye, for adding a prism degree to the eye; rotation means including a pulse motor and a rotation transmitting mechanism for transmitting rotation of the pulse motor to the rotary prism, the rotation means being adapted for rotating the rotary prism to change the prism degree; command means for generating a command signal to start and stop the rotation of the rotary prism; and control means for controlling the rotation means to drive the pulse motor to rotate at a speed of 5 pulses/sec. or more when the control means receives the rotation start command signal until when receives the rotation stop command signal, and, to change the prism degree at a speed of 0.1 to 1.0 prism/sec.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
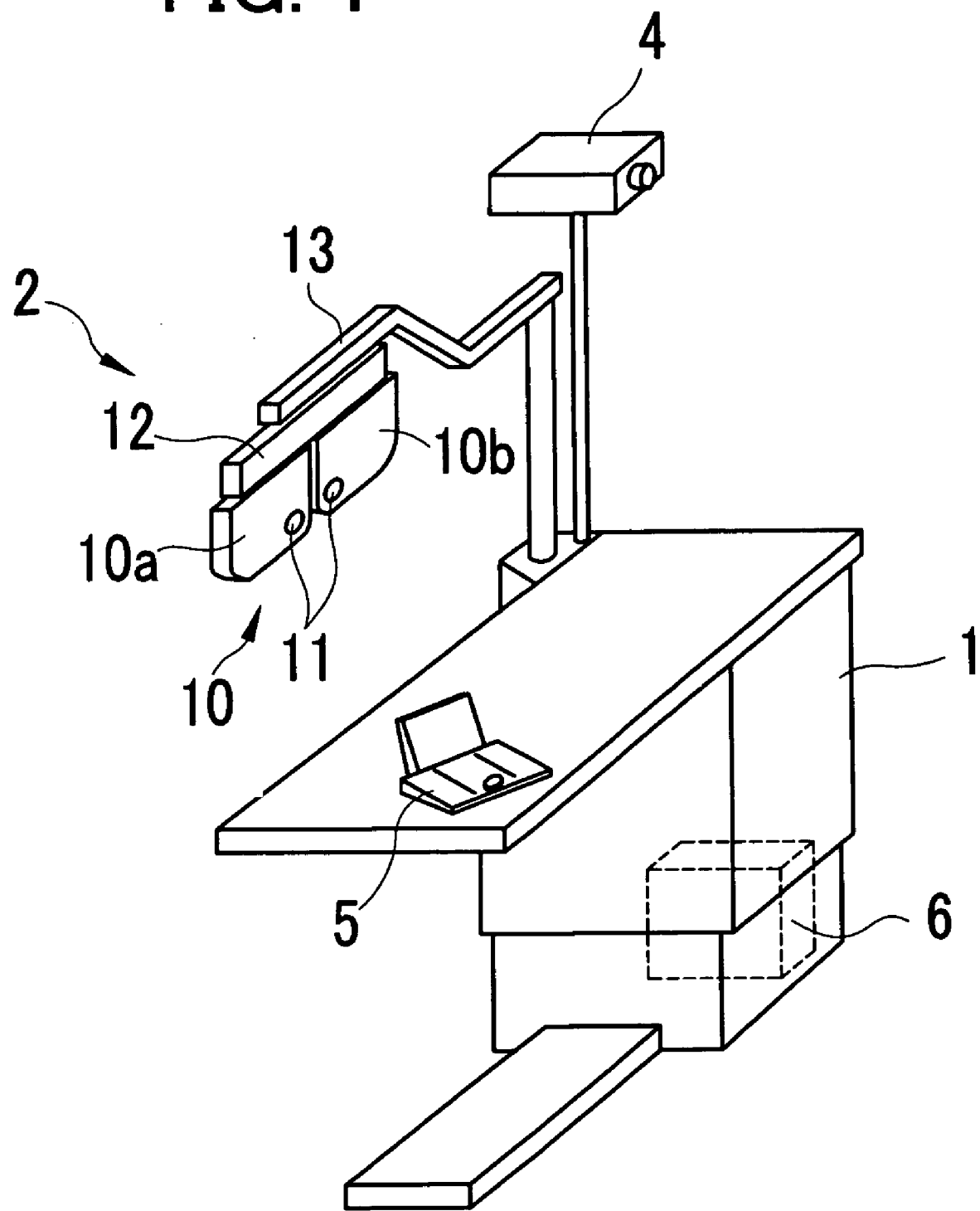
FIG. 1 is a general view of a structure of an optometric system.

A detailed description of a preferred embodiment of an optometric apparatus embodying the present invention will now be given referring to the accompanying drawings. FIG. 1 is a general view of a structure of an optometric system in the present embodiment.

A subjective-type optometric apparatus 2 is provided with a pair of lens chamber units 10 which are symmetrically constructed for a right and left eyes, in each of which includes a test window 11 in which various kinds of optical elements are electrically selectively disposed, and a support unit 12 which supports (holds) the lens chamber units 10. The support unit 12 is supported on a table 1 through an arm 13. It is to be noted that the lens chamber units 10 include a lens chamber unit 10a for a right eye examination and a lens chamber unit 10b for a left eye examination.

The optometric system is further provided with an optotype presenting apparatus 4, a controller 5, and a relay unit 6. The presenting apparatus 4 is used to present examination optotypes by projection. The controller 5 is used to operate the optometric apparatus 2 and the presenting apparatus 4. The relay unit 6 is to relay transmission between the apparatuses.

Figure 2:
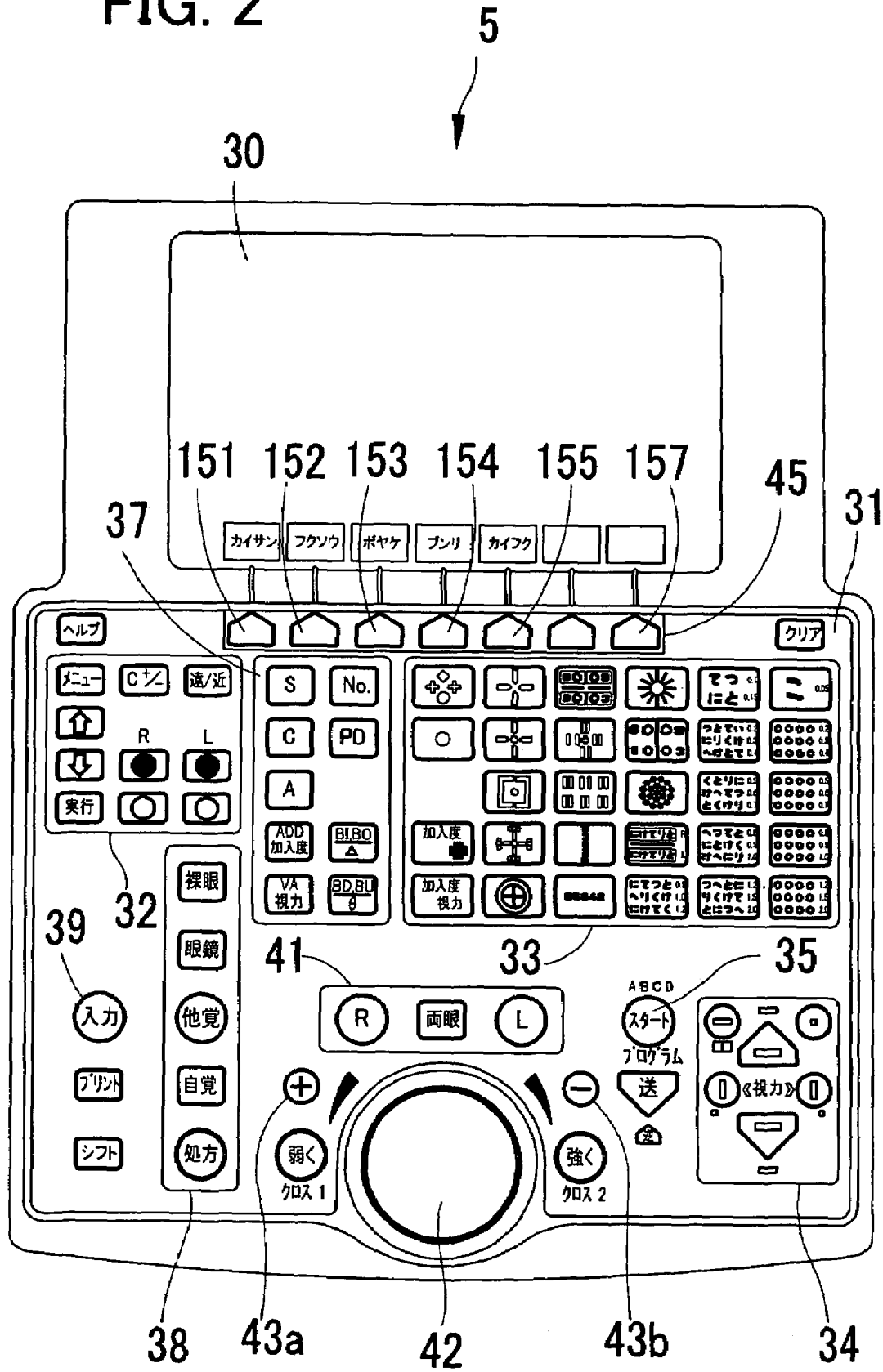
FIG. 2 is a top view of a controller.

FIG. 2 is a top view of the controller 5. This controller 5 is provided with a display 30 and a switch section 31. The display 30 is a liquid crystal display for displaying information or data on eye examinations and others. The switch section 31 includes a group of setting switches 32, a group of optotype switches 33, a group of mask switches 34, a start switch 35, groups of designation switches 37, 38, and 41, a data input switch 39, switches 43a and 43b, a dial switch 42, and a group of function switches 45.

In the present embodiment, the setting switches 32 are used to change a display screen of the display 30 to a menu screen for setting parameters and so on. The optotype switches 33 are used to change (select) optotypes to be presented by the presenting apparatus 4. The mask switches 34 are used to change (select) masks to be applied to a part of the selected optotypes to be presented. The start switch 35 is used to execute eye examinations previously programmed. The designation switches 37 are used to designate a mode for examination data and others. The designation switches 38 are used to designate a data input mode or an examination mode. The data input switch 39 is used to input data from an objective type eye refractive power measuring apparatus 3, a lens meter 9, etc. The designation switches 41 are used to designate an eye to be examined.

The switches 43a and 43b are used in a cross-cylinder examination, and a divergence examination and a convergence examination which use a rotary prism. In the divergence examination and the convergence examination, the push of the switch 43a causes the rotary prism to rotate in a direction that increases the prism degree, and, on the other hand, the push of the switch 43b causes the rotary prism to rotate in the opposite direction that decreases the prism degree. Those switches 43a and 43b are also used as means for inputting a switch signal for stopping changing (increase/decrease) of the prism degree. The dial switch 42 is used to change measured values and input numeric values. This switch 42 is also used to designate the prism degree in the divergence examination and the convergence examination. The function switches 45 are used to select an associated one with various switch displays appear on the screen of the display 30 at a predetermined lower position.

Figure 3:
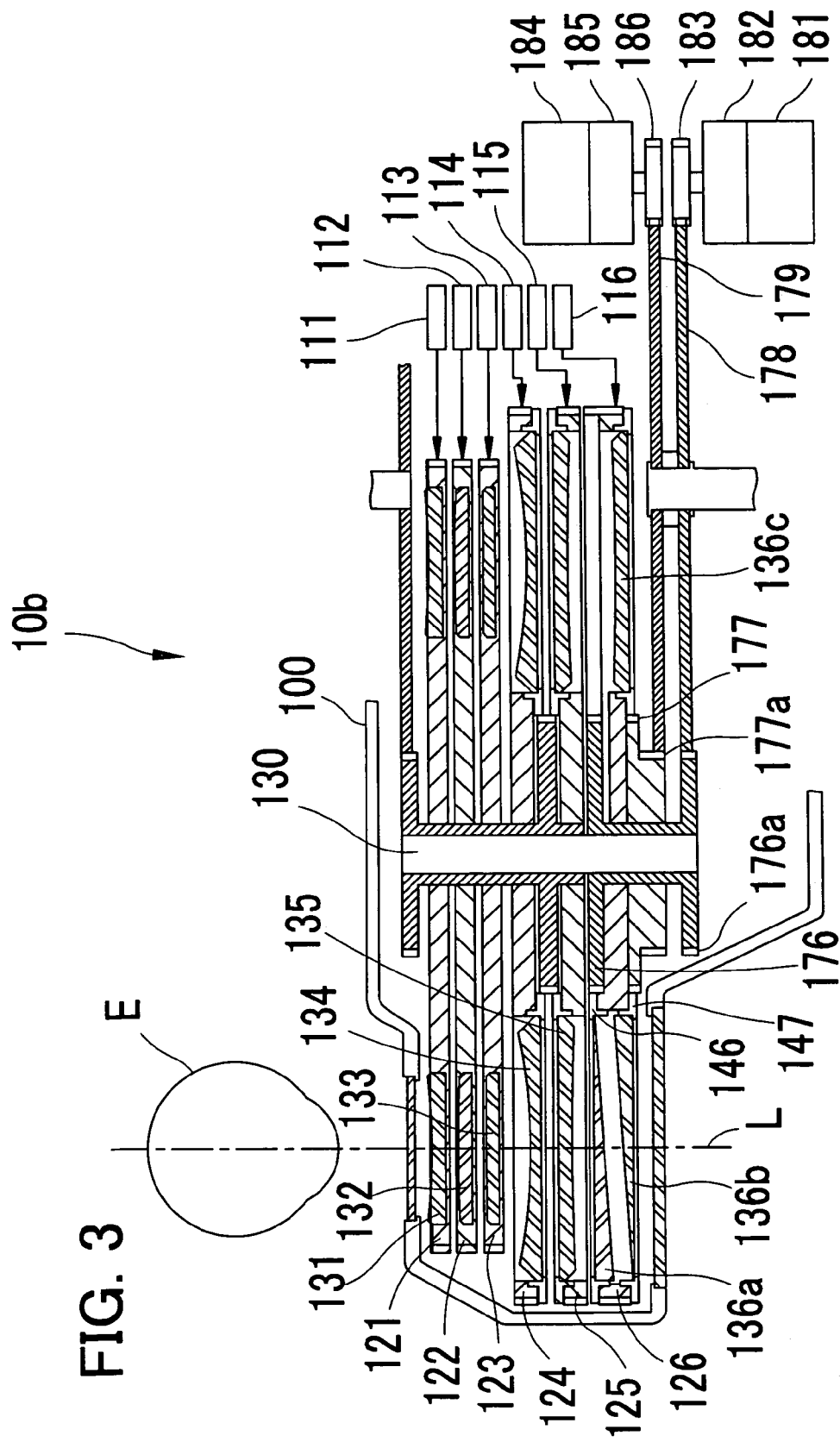
FIG. 3 is a sectional view of a part of a lens chamber unit for a left eye, viewed from above.

FIG. 3 is a schematic sectional view of a part of the lens chamber unit 10b for a left eye, viewed from above. "L" is an examination optical axis. "E" is the left eye of an examinee. The lens chamber unit 10b includes a cover 100, in which six rotary disks 121–126 are placed (held) to be rotatable about a shaft 130. In each rotary disk 121–126, an opening and a plurality of optical elements are set (held). These rotary disks are arranged in the following order from nearer to farther with respect to the eye E; a high-power spherical lens disk 121, a low-power spherical lens disk 122, a first auxiliary lens disk 123, a high-power cylindrical lens disk 124, a low-power cylindrical lens disk 125, and a second auxiliary lens disk 126. Each disk 121–126 has an outer periphery formed with gear teeth and is rotated by operation of an associated one of pulse motors 111–116, thus changing an optical element to be disposed on the optical axis L.

Each disk 121–126 has at least one opening with no lens or with a lens of 0 D (diopter). The disk 121 holds eleven spherical lenses 131 of different high powers (refractive powers); −3 D, −6 D, −9 D, −12 D, −15 D, −18 D, +3 D, +6 D, +9 D, +12 D, and +15 D. The disk 122 holds eleven spherical lenses 132 of different low powers (refractive powers); −0.25 D, −0.5 D, −0.75 D, −1 D, +0.25 D, +0.5 D, +0.75 D, +1 D, +1.25 D, +1.5 D, and +1.75 D. The disk 123 holds auxiliary lenses 133 including a shielding plate (BL), a polarizing plate (P135, P45), a Maddox lens (MR), a pinhole (PH), a red/green filter (R/G), a dispersion prism (6/10Δ), a plain lens (PD) with a mark for adjustment of an interpupillary distance (the interval between the right and left lens chamber units 2) according to the examinee's pupillary distance, a spherical lens of −10 D, and a spherical lens of +10 D.

The disk 124 holds five cylindrical lenses 134 of different high powers (refractive powers); −1.5 D, −3 D, −4.5 D, −6 D, −7.5 D. The disk 125 holds five cylindrical lenses 135 of different low powers (refractive powers); −0.25 D, −0.5 D, −0.75 D, −1 D, −1.25 D. The disk 126 holds auxiliary lenses such as rotary prisms 136a and 136b, a cross-cylinder lens 136c, and others. The rotary prisms 136a and 136b and the cross-cylinder lens 136c are placed to be individually rotatable about the optical axis L. The rotary prisms 136a and 136b are constructed of a pair of prisms having the same degree which are connected with each other through gears or the like. These prisms 136a and 136b are rotated at equal angles in opposite directions, thereby changing the prism degree.

Next, a rotation mechanism of the rotary prisms 136a and 136b is explained. The rotary prism 136a is held in the disk 126 through a holder 146 having gear teeth so that the rotary prism 136a is rotatable about the optical axis L. The gear teeth of the holder 146 engage with a sun gear 176 which is rotatable about the shaft 130. Thus, the rotation of a pulse motor 181 is transmitted to the rotary prism 136a through a relay gear 178 and a gear 176a connected with the sun gear 176. The pulse motor 181 is attached with a gear head 182 which provides a speed reducing ratio of 1/30. A gear 183 fixed to an output shaft of the gear head 182 engages with the relay gear 178.

The rotary prism 136b is held in the disk 126 through a holder 147 having gear teeth, at the opposite side of the rotary prism 0.136a (in other words, at the farther side from the eye E) so that the rotary prism 136b is rotatable about the optical axis L. The gear teeth of the holder 147 engage with a sun gear 177 which is rotatable about the shaft 130. Thus, the rotation of a pulse motor 184 is transmitted to the rotary prism 136b through a relay gear 179 and a gear 177a connected with the sun gear 177. The pulse motor 184 is attached with a gear head 185 which provides a speed reducing ratio of 1/30. A gear 186 fixed to an output shaft of the gear head 185 engages with the relay gear 179.

The above gear heads 182 and 185 and the above gears constitute a rotation transmitting mechanism for transmitting the speed of rotation of the pulse motors 181 and 184 while reducing the speed to the rotary prisms 136a and 136b. This rotation transmitting mechanism is constructed so that the prism degree is changed in steps of 0.05 prism or less, more preferably, 0.01 prism or less, by the rotation of the rotary prisms 136a and 136b (the pulse motors 181 and 184).

It is to be noted that the lens chamber unit 10a for a right eye examination is identical in structure to the lens chamber unit 10b for a left eye examination and hence the explanation thereof is omitted herein.

Figure 4:
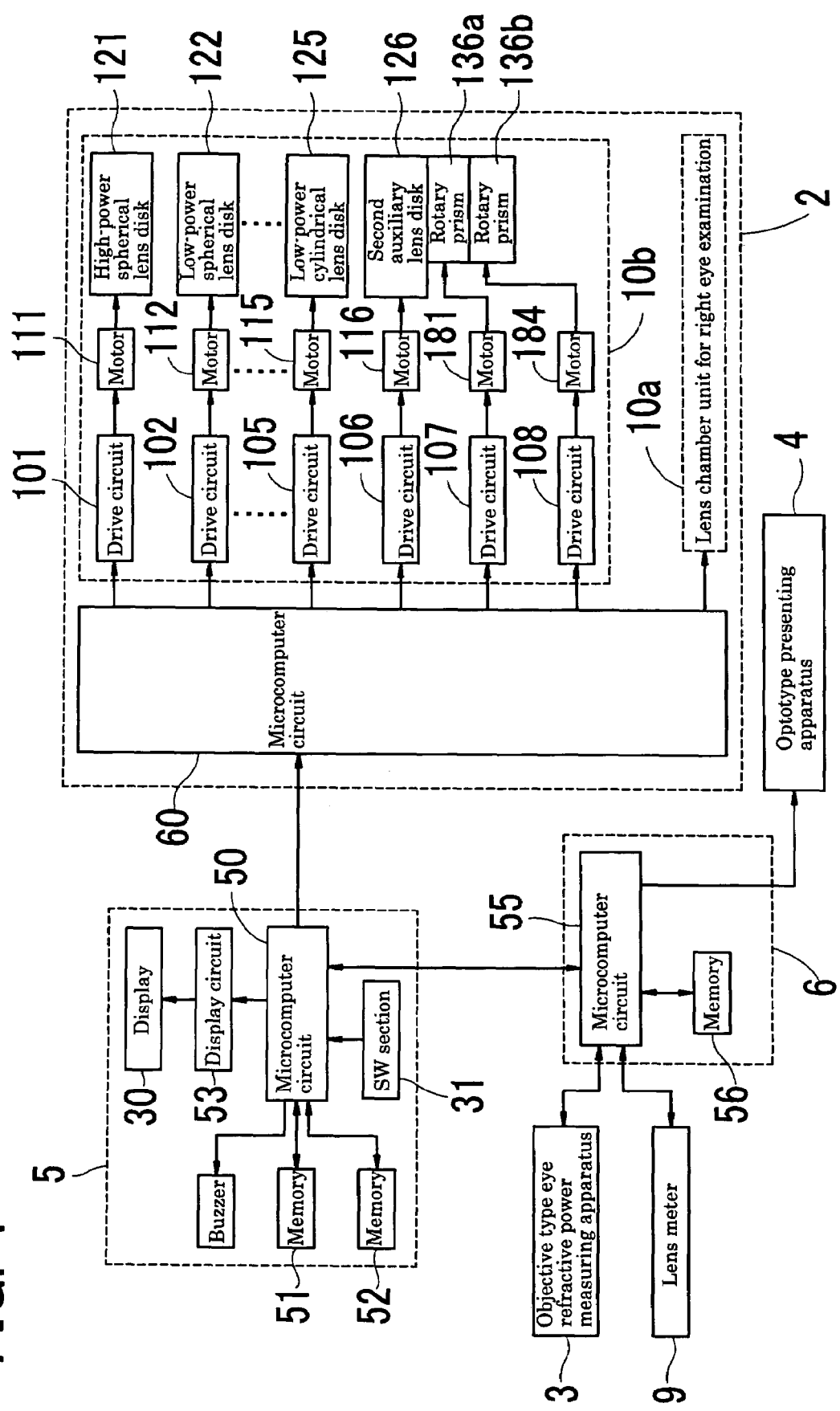
FIG. 4 is a schematic block view of a control system of the optometric system.

FIG. 4 is a schematic block diagram of a control system of the optometric system in the present embodiment. A switch signal from a switch section 31 on the controller 5 is subjected to a predetermined processing and then inputted to a microcomputer circuit 50. The microcomputer circuit 50 is connected to a memory 51 which previously stores a control program such as an eye examination program and a memory 52 which stores data on measured values in an objective refractive power examination. The microcomputer circuit 50 converts the switch signal to various kinds of data signals based on the control program stored in the memory 51 and controls the screen of the display 30 through a display circuit 53. Furthermore, the microcomputer circuit 50 transmits the converted data signals to a microcomputer circuit 55 in the relay unit 6 and transmits data signals representing a refractive power and movements of the lens chamber unit 10 to the optometric apparatus 2. The microcomputer circuit 55 transmits a data signal representing optotypes to the presenting apparatus 4.

Upon receipt of the data signal representing the refractive power, a microcomputer circuit 60 in the optometric apparatus 2 controls the lens chamber units 10a and 10b respectively. For the lens chamber unit 10b, the microcomputer circuit 60 drives a pulse motor 111 through a drive circuit 101 to rotate the disk 121, disposing a predetermined optical system in the test window 11. Similarly, the microcomputer circuit 60 drives pulse motors 112 to 116 through drive circuits 102 to 106 respectively to rotate the disks 122 to 126, disposing a predetermined optical element in the test window 11. When receiving a data signal to change the prism degree, then, the microcomputer circuit 60 drives the pulse motors 181 and 184 through drive circuits 107 and 108 to rotate the rotary prisms 136a and 136b. It is to be noted that the lens chamber unit 10a is controlled in the same manner.

The presenting apparatus 4, when received the data signal representing optotype(s), projects predetermined optotype(s) on a screen not shown placed forward of the eye E.

The microcomputer circuit 55 is connected with the objective type eye refractive power measuring apparatus 3 and the lens meter 9, and stores measurement data transmitted therefrom in a memory 56. When receiving a readout command signal from the microcomputer circuit 50, the microcomputer circuit 55 reads out the designated measurement data from the memory 56 and transmits it to the controller 5.

The operation of the optometric system constructed as above is explained below.

The eye examination program is first executed at the push of the start switch 35. This program, which is stored in advance in the memory 51 as mentioned above, includes previously set examination items and an examination flow. In the present embodiment, explanation is made on the operation in the divergence examination and the convergence examination after full correcting powers are prescribed for both eyes in the subjective examination using a program for the subjective eye examination.

[Divergence Examination]

When a "カイサン"(Divergence) key 151 of the function keys 45 is pressed, the rotary prisms 136a and 136b are disposed in the test windows 11 for the right and left eyes respectively so that each prism base direction becomes a B.I.(Base In)/B.O.(Base Out) direction. The optotypes of minimum-sized characters which an examinee can correctly read or of slightly larger characters than the minimum-sized ones are presented in a vertical row.

In the divergence examination, when the switch 43a is pushed, the microcomputer circuit 50 transmits a command signal to the microcomputer circuit 60 to start the rotation of the rotary prism 136a and 136b in the direction that increases the B.I. prism degree. The microcomputer circuit 60 thus causes the pulse motors 181 and 184 to start to operate. Then, when the switch 43a is pushed again, the microcomputer circuit 50 transmits a command signal to the microcomputer circuit 60 to stop the rotation of the rotary prisms 136a and 136b. The microcomputer circuit 60 thus causes the pulse motors 181 and 184 to stop operating. When the switch 43b is pushed, on the other hand, the microcomputer circuit 50 transmits a command signal to the microcomputer circuit 60 to start the rotation of the rotary prisms 136a and 136b in the direction that decreases the B.I. prism degree. Then, when the switch 43b is pushed again, the microcomputer circuit 50 transmits a command signal to the microcomputer circuit 60 to stop the rotation of the rotary prisms 136a and 136b.

For rotating the rotary prisms 136a and 136b, the microcomputer circuit 60 outputs a driving pulse signal to drive the pulse motors 181 and 184 to rotate at a speed of 5 pulses/sec. or more and to slowly change the prism degree at a speed of 0.1 to 1.0 prism/sec. When the pulse motors 181 and 184 are driven to rotate at a speed of 5 pulses/sec. or more, the prism degree will change at 5 times/sec. or more. This makes it possible to make the optotypes appear to smoothly changes in succession. Further, the changing of the prism degree at the speed of 0.1 to 1.0 prism/sec. allows an examiner to easily check the examinee's response in the examination. At this time, the rotation of the rotary prisms 136a and 136b (the pulse motors 181 and 184) is controlled so that the prism degree is changed in steps of 0.05 prism or less, more preferably, 0.01 prism or less. For example, if the rotation transmitting mechanism is constructed such that the change step of the prism degree is 0.01 prism/pulse, the pulse motors 181 and 184 are driven to rotate at a speed of 10 to 100 pulses/sec. Thus, the prism degree can be changed at a speed of 0.1 to 1.0 prism/sec., achieving smooth changes of the prism degree and easy checks of the examinee's response. It is to be noted that this speed is set in advance with the function switch 157. At the push of this switch 157, the changing speed of the prism degree can be set in a range of 0.1 to 1.0 prism/sec.

The examiner pushes the switch 43a once, starting the rotation of the rotary prisms 136a and 136b to slowly continuously increase the B.I. prism degree, and asks the examinee about whether the optotype appears blurred. When the examinee responds that the optotype appears blurred, the examiner pushes the switch 43a, stopping the rotation of the rotary prisms 136a and 136b, and then pushes a "ボヤケ"(Blur) key 153 of the function key 45 to store a value of the prism degree at that time in the memory 52.

Subsequently, the examiner pushes the switch 43a once, further slowly continuously increasing the B.I. prism degree, and asks the examinee about whether the optotype appears double. At the time when the examinee responds that the optotype appears double, the examiner pushes the switch 43a and pushes a "ブンリ"(Break) key 154 of the function key 45 to store a value of the prism degree at that time in the memory 52.

Next, the examiner pushes the switch 43b, continuously slowly decreasing the B.I. prism degree, and asks the examinee about whether the optotype appears (has returned to) single. At the time when the examinee responds that the optotype appears single, the examiner pushes a "カイフク"(Recovery) key 155 of the function key 45 to store the prism degree value at that time in the memory 52.

[Convergence Examination]

When a "フクソウ"(Convergence) key 152 of the function key 45 is pushed, the rotary prisms 136a and 136b are disposed in the test windows 11 for both eyes so that the prism base direction becomes the B.I./B.O. direction. In addition, the optotypes of minimum-sized characters which the examinee can correctly read or of slightly larger characters than the minimum-sized ones are presented in a vertical row.

In the convergence examination, when the switch 43b is pushed, the microcomputer circuit 50 transmits a command signal to the microcomputer circuit 60 to start the rotation of the rotary prisms 136a and 136b in the direction that increases the B.O. prism degree. When the switch 43a is pushed, on the other hand, the microcomputer circuit 50 transmits a command signal to the microcomputer circuit 60 to start the rotation of the rotary prisms 136a and 136b in the direction that decreases the B.O. prism degree. When the switches 43b and 43a are pushed again respectively, the microcomputer circuit 50 transmits a command signal to the microcomputer circuit 60 to stop the rotation of the rotary prisms 136a and 137b.

The examiner pushes the switch 43b once to start the rotation of the rotary prisms 136a and 136b, continuously slowly increasing the B.O. prism degree, and asks the examinee about whether the optotype appears blurred. At the time when the examinee responds that the optotype appears blurred, the examiner pushes the switch 43b to stop the rotation of the rotary prisms 136a and 136b and then pushes the "ボヤケ"(Blur) key 153 of the function key 45 to store the prism degree at that time in the memory 52.

Subsequently, the examiner pushes the switch 43b once, further continuously slowly increasing the B.O. prism degree, and asks the examinee about whether the optotype appears double. At the time when the examinee responds that the optotype appears double, the examiner pushes the switch 43b again and additionally pushes the "ブンリ"(Break) key 154 of the function key 45 to store the prism degree in the memory 52.

Next, the examiner pushes the switch 43a once, continuously slowly decreasing the B.O. prism degree, and asks the examinee about whether the optotype appears (has returned to) single. At the time when the examinee responds that the optotype appears single, the examiner pushes the switch 43a and additionally pushes the "カイフク"(Recovery) key 155 of the function key 45 to store the prism degree at that time in the memory 52.

The input of the command signal to start/stop the rotation of the rotary prisms 136a and 136b is not limited to the above manner and alternatively may be made as follows. It is constructed such that the command signal to start the rotation is input when the switch 43a or 43b is pushed and the command signal to stop the rotation is input when the switch 43a or 43b is released. While the switch 43a or 43b is being pushed, the microcomputer circuit 60 drives the pulse motors 181 and 184 to continuously rotate the rotary prisms 136a and 136b.

As described above, the rotation transmitting mechanism such as the gear heads 182 and 185 and others are operated to reduce the speed of rotation of the pulse motors 181 and 184. Thus, the rotation step angle of the rotary prisms 136a and 136b becomes minute in accordance with the speed reducing ratio (1/30) of the gear heads 182 and 185. The change step of the prism degree is set to 0.05 prism or less, more preferably 0.01 prism or less, so that the prism degree can be changed smoothly even when the prism degree changes at a slow speed of 0.1 to 1.0 prism/sec.

Further, it is constructed that the microcomputer circuit 60 drives the pulse motors 181 and 184 when receiving the rotation start command signal until when receiving the rotation stop command signal. Accordingly, it does not take much time for signal processing to change the prism degree as compared with the conventional apparatus and also it is possible to continuously change the prism degree.

In the divergence examination and the convergence examination, it is preferable to largely change at first to some extent and then slowly change. This makes it possible to efficiently perform examinations. In particular, in the convergence examination, normally, many examinees each have about 20 prisms for both eyes. In this case, the dial switch 42 is operated to previously designate the prism degree (for example 15 prisms) to be added to the eye E. For instance, when the microcomputer circuit 50 transmits a signal designating the prism degree from the dial switch 42 to the microcomputer circuit 60, the microcomputer circuit 60 drives the pulse motors 181 and 184 to rotate at a speed faster than 0.1 to 1.0 prism/sec. If the change step of the prism degree per one pulse of the pulse motors 181 and 184 is set at 0.01 prism/pulse and the pulse motors 181 and 184 are driven to rotate at a speed of 1000 pulses/sec., the prism degree for one eye can be changed at a speed of 10 prism/sec. And then, the switches 43a and 43b are used to slowly change the prism degree, thereby smoothly changing the prism degree in a similar manner to in a subjective type eye examination apparatus (a refractor) manually operated. Further, the examinations can be performed promptly and correctly.

As explained above, according to the present invention, the prism degree can be smoothly changed and the visual function examinations can be accurately conducted.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometric apparatus for subjectively examining visual functions of an eye of an examinee, the apparatus including:
    a rotary prism disposed in front of the eye, for adding prism power to the eye;
    rotation means including a pulse motor and a rotation transmitting mechanism for transmitting rotation of the pulse motor to the rotary prism, the rotation means being adapted for rotating the rotary prism to change the prism power to be added to the eye;
    the rotation transmitting mechanism including a gear mechanism having a predetermined speed reducing ratio, which transmits the rotation of the pulse motor to the rotary prism while reducing a rotation speed of the pulse motor so as to reduce a rotation step angle of the rotary prism with respect to a rotation step angle of the pulse motor so that a change step of the prism power is 0.05 prism diopter or less to make the prism power to be added to the eye appear to smoothly change, and
    command means for generating a command signal to start and stop the rotation of the rotary prism; and
    control means for driving the pulse motor to rotate at a speed of 5 to 100 pulses/sec. when the control means receives the rotation start command signal until when the control means receives the rotation stop command signal so that a change speed of the prism power is 0.1 to 1.0 prism diopter/sec. to make the prism power to be added to the eye appear to slowly change.

2. The optometric apparatus according to claim 1 further including setting means for setting the change speed of the prism power in a range of 0.1 to 1.0 prism diopter/sec.

3. The optometric apparatus according to claim 1 further including designation means for designating the prism power to be added to the eye,
    wherein the control means, when the control means receives the designation signal from the designation means, the control means drives the pulse motor so that the prism power changes at a speed faster than 1.0 prism diopter/sec. up to the designated prism power.

4. An optometric apparatus for subjectively examining visual functions of an eye of an examinee, the apparatus including:
    a rotary prism disposed in front of the eye, for adding prism power to the eye;
    a rotation unit which includes a pulse motor and a rotation transmitting mechanism for transmitting rotation of the pulse motor to the rotary prism, the rotation unit being adapted for rotating the rotary prism to change the prism power to be added to the eye;
    the rotation transmitting mechanism including a gear mechanism having a predetermined speed reducing ratio, which transmits the rotation of the pulse motor to the rotary prism while reducing a rotation speed of the pulse motor so as to reduce a rotation step angle of the rotary prism with respect to a rotation step angle of the pulse motor so that a change step of the prism power is 0.05 prism diopter or less to make the prism power to be added to the eye appear to smoothly change, and a command device which generates a command signal to start and stop the rotation of the rotary prism; and a control unit which drives the pulse motor to rotate at a speed of 5 to 100 pulses/sec. when the control unit receives the rotation start command signal until when the control unit receives the rotation stop command signal so that a change speed of the prism power is 0.1 to 1.0 prism diopter/sec. to make the prism power to be added to the eve appear to slowly change.

* * * * *